(12) United States Patent
Emery et al.

(10) Patent No.: US 11,160,576 B1
(45) Date of Patent: Nov. 2, 2021

(54) AMPUTATION SYSTEM FOR FIELD USE

(71) Applicant: The United States of America as Represented by the Secretary of the Navy, Indian Head, MD (US)

(72) Inventors: Samuel Emery, Alexandria, VA (US); Lee Foltz, Indian Head, MD (US); Daniel McCarthy, LaPlata, MD (US); Keith Chamberlain, Waldorf, MD (US); Kerry Clark, LaPlata, MD (US); Peter A. Margiotta, LaPlata, MD (US); Matthew Bradley, Columbia, MD (US); David R. Whittaker, Potomac, MD (US); Erin E. Koelling, Washington, DC (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 16/873,765

(22) Filed: Jun. 29, 2020

(51) Int. Cl.
| | |
|---|---|
| *A61B 17/32* | (2006.01) |
| *A61B 17/17* | (2006.01) |
| *A61B 17/16* | (2006.01) |
| *A61B 17/00* | (2006.01) |

(52) U.S. Cl.
CPC .......... *A61B 17/32* (2013.01); *A61B 17/1628* (2013.01); *A61B 17/17* (2013.01); *A61B 2017/00477* (2013.01); *A61B 2017/320052* (2013.01)

(58) Field of Classification Search
CPC ... A61B 17/32–326; A61B 2017/32004–3225; A61B 17/16–1697; A61B 2017/1602–1653; B26D 1/006; B26D 1/04; B26D 1/08; B26D 1/085; B26D 1/147; B26D 1/18; B26D 3/001; B26D 3/008; B26D 3/166; B26D 3/167
See application file for complete search history.

(56) References Cited

U.S. PATENT DOCUMENTS

| | | | |
|---|---|---|---|
| 2,711,583 A | | 6/1954 | Raby |
| 3,306,297 A | * | 2/1967 | Baylor ............... A61B 17/3215 128/207.29 |
| 4,412,380 A | | 11/1983 | Kish |
| 4,434,555 A | * | 3/1984 | Stoll ...................... B26D 3/169 30/179 |
| 4,608,754 A | * | 9/1986 | Kloster .................. B23D 21/00 30/92 |
| 4,654,999 A | | 4/1987 | Raggett |
| 4,769,944 A | | 9/1988 | Fresne et al. |

(Continued)

*Primary Examiner* — Matthew J Lawson
(74) *Attorney, Agent, or Firm* — Fredric J. Zimmerman

(57) ABSTRACT

An amputation system includes a cutting element having a cutting blade traversing a V-shape. The V-shape has a vertex and an angle in a range of 90-120°. A rod, rigidly coupled to the cutting element, has its longitudinal axis aligned with the vertex so it bisects the angle of the V-shape. A barrel having a bore receives at least a portion of the rod therein wherein the rod's outboard end resides in the bore. An energetic energy source, positioned in the bore adjacent to the rod's outboard end, generates a pressure force that is incident on the rod's outboard end. The pressure force is one that peaks within 0.5 milliseconds to propel the rod from the bore at a velocity in a range of 300 to 1000 feet per second.

10 Claims, 2 Drawing Sheets

(56) References Cited

U.S. PATENT DOCUMENTS

| | | | | |
|---|---|---|---|---|
| 5,018,275 | A | * | 5/1991 | Huang .................... B26B 13/26 30/124 |
| 5,070,616 | A | * | 12/1991 | Chen ........................ B26D 5/12 30/92 |
| 5,125,158 | A | | 6/1992 | Casebolt et al. |
| 5,711,078 | A | * | 1/1998 | Patton .................... B26B 15/00 30/182 |
| 6,277,135 | B1 | * | 8/2001 | Wang ............... A61B 17/32002 30/316 |
| 6,391,031 | B1 | * | 5/2002 | Toomey ................. A61B 17/15 606/82 |
| 7,461,457 | B2 | * | 12/2008 | Liverman ................ B26D 1/08 30/180 |
| 2011/0004214 | A1 | * | 1/2011 | Skaggs .............. A61B 17/1671 606/84 |
| 2012/0283793 | A1 | * | 11/2012 | Burroughs, III ... A61B 17/3205 606/86 R |
| 2013/0000932 | A1 | | 1/2013 | Corsini et al. |

* cited by examiner

AMPUTATION SYSTEM FOR FIELD USE

ORIGIN OF THE INVENTION

The invention described herein was made in the performance of official duties by employees of the Department of the Navy and may be manufactured, used, licensed by or for the Government for any governmental purpose without payment of any royalties thereon.

FIELD OF THE INVENTION

The invention relates generally to amputation devices for limbs or extremities, and more particularly to an amputation system for use in non-surgical field settings.

BACKGROUND OF THE INVENTION

In hospital settings, extremity and limb amputations are performed by a team of doctors and nurses in a sterile environment using the latest in medical technology while a patient is under sedation. Further, most surgical amputations are planned procedures. Unfortunately, in battlefield situations, the only thing that an amputation procedure has in common with a surgical amputation is the need for a patient to have the amputation performed. In addition, field amputations are generally performed in life-or-death situations where time is of the essence.

Currently, field-based amputations are performed using legacy tools. For example, combat medical personnel are equipped with field medical kits that include rudimentary handsaws that are comparable to those used during the Civil War and/or rudimentary wire saws comparable to those used to cut tree limbs. In an urgent and/or life threatening situation where a limb has been pinned or partially amputated via catastrophic trauma, a disarticulation or guillotine amputation may be employed. In this process, the field medic or surgeon would conduct the guillotine amputation utilizing the hand or wire saw. This is a hand-controlled process. The amputation is conducted above the trauma or pinned portion of the extremity, and may be conducted either at a joint or through a segment of bone. Depending on the extremity, where the amputation will occur, and outside factors such as combat, the time needed may be between 10-40 minutes and can require a tourniquet if ligation of blood vessels is not feasible. Under the current method, additional blood loss occurs and the time between casualty and receiving critical care is increased. Thus, in general, current field-based amputations are both slow and traumatic.

SUMMARY OF THE INVENTION

Accordingly, it is an object of the present invention to provide an amputation system.

Another object of the present invention is to provide an amputation system capable of performing a quick and clean severing of a damaged extremity or limb to reduce the trauma level experienced by a patient.

Still another object of the present invention is to provide an amputation system that greatly improves all facets of an amputation performed in a field setting.

Other objects and advantages of the present invention will become more obvious hereinafter in the specification and drawings.

In accordance with the present invention, an amputation system includes a cutting element having a cutting blade traversing a V-shape. The V-shape has a vertex and has an angle in a range of 90-120°. A rod is rigidly coupled to the cutting element. The rod has a longitudinal axis aligned with the vertex and bisects the angle. The rod has an outboard end. A barrel having a bore receives at least a portion of the rod therein wherein the outboard end of the rod resides in the bore. An energetic energy source is positioned in the bore adjacent to the outboard end of the rod. The energetic energy source generates a pressure force that is incident on the outboard end of the rod. The pressure force is one that peaks within 0.5 milliseconds to propel the rod from the bore at a velocity in a range of 300 to 1000 feet per second.

BRIEF DESCRIPTION OF THE DRAWINGS

Other objects, features and advantages of the present invention will become apparent upon reference to the following description of the exemplary embodiments and to the drawings, wherein corresponding reference characters indicate corresponding parts throughout the several views of the drawings and wherein.

DETAILED DESCRIPTION OF THE INVENTION

Figure 1:
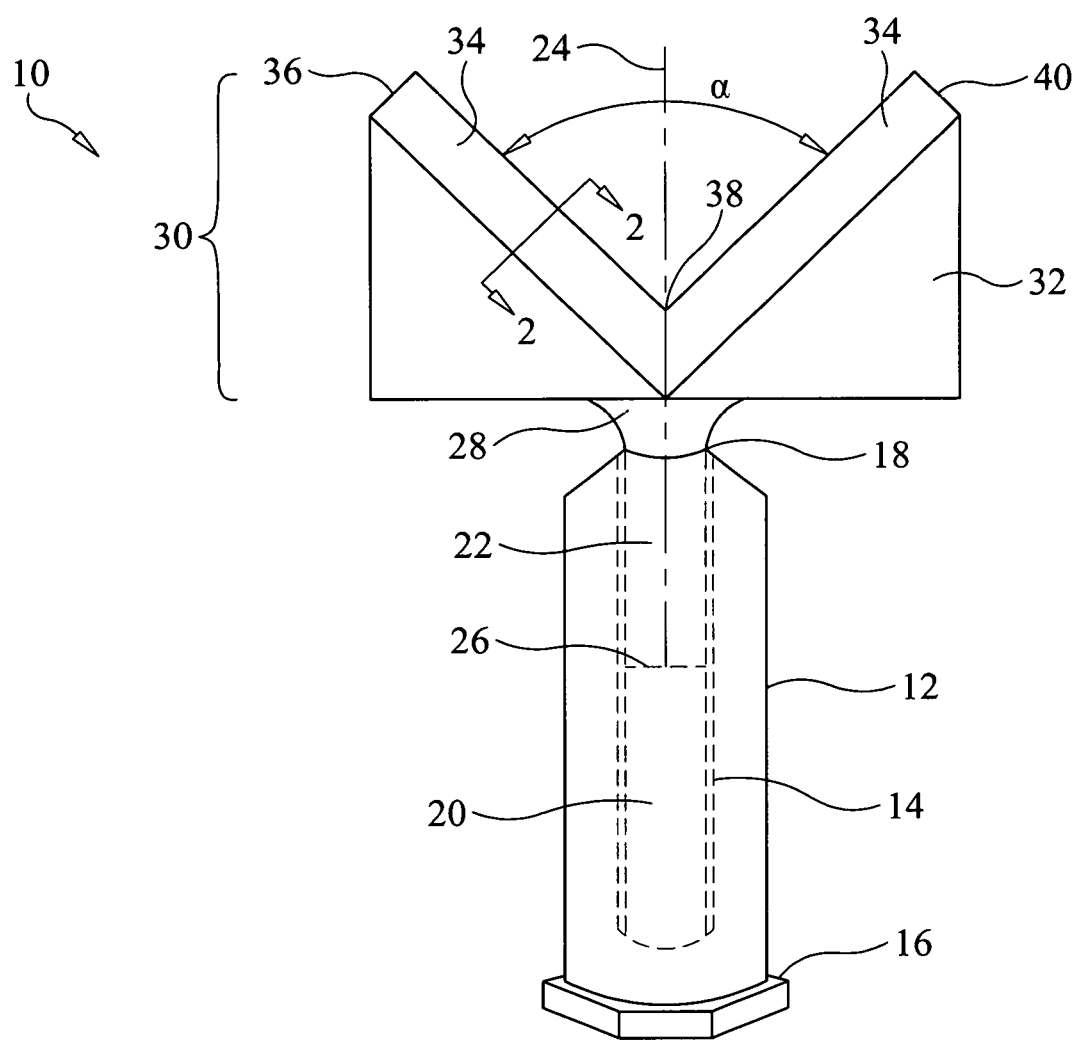
FIG. 1 is a perspective view of an amputation system in accordance with an embodiment of the present invention.

Referring now to the drawings and more particularly to FIG. 1, an amputation system in accordance with the present invention is shown and is referenced generally by numeral 10. While amputation system 10 can be used in hospital and field settings, system 10 greatly improves the equipment and procedures associated with field amputations where a patient's limb needs to be severed quickly and cleanly as part of life-saving emergency care.

Amputation system 10 includes a launch barrel 12 having an internal bone 14 that is closed at end 16 and open at end 18. Mounted in bore 14 near closed end 16 is an energy source 20 capable of generating a launch or propulsion force as will be described later herein. Also disposed in bore 14 is a drive rod 22 that slidingly fits in bore 14 and extends from open end 18 thereof such that the longitudinal axis 24 of drive rod 22 is coincident with the longitudinal axis launch barrel 12. One end 26 of drive rod 22 will receive the above-described propulsion force of energy source 20. The other end 28 of drive rod 22 is rigidly coupled (e.g., integrated) with a cutting element 30.

Cutting element 30 includes a support body 32 rigidly coupled to end 28 of drive rod 22 and a cutting blade 34 rigidly coupled (e.g., integrated) with support body 32. Since most or all of cutting blade 34 will make the severing contact with a patient during an amputation procedure, cutting blade 34 is made from a rigid medical grade material such as medical-grade stainless steels, titanium, etc., the choice of which is not a limitation of the present invention. Furthermore, since some or all of support body and, possibly, drive rod 22 will likely contact the patient immediately following the severing contact made by cutting blade 34, medical grade material could also be used for both support body 32 and drive rod 22.

Cutting blade 34 traverses a V-shape all along its length that extends from one outboard edge 36 to a vertex 38 and then to another outboard edge 40. The angle α defined by the blade's V-shape is in the range of 90-120°. This range of angles allows the regions of cutting blade 34 near outboard edges 36/40 to cut through soft tissue before the regions of cutting blade 34 near vertex 38 cut through hard/bone tissue as will be explained further below.

Figure 2:
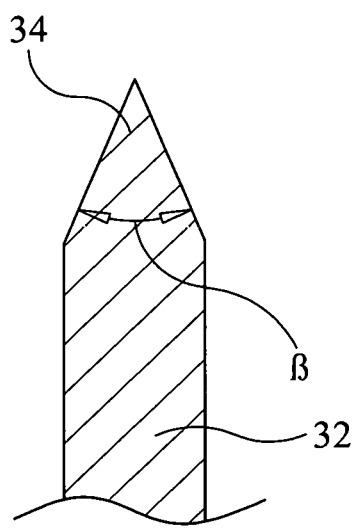
FIG. 2 is a cross-sectional view of the amputation system's cutting blade taken along line 2-2 in FIG. 1.

To provide a uniform cutting action, the cross-section of cutting blade 34 may be the same or constant all along its length from outboard edge 36 to outboard edge 40. More specifically and as shown in FIG. 2, the cross-section of cutting blade 34 taken perpendicular to cutting blade 34 remains constant. The taper angle β of cutting blade 34 is in the range of 15-25° to support cutting of both soft and hard tissue.

As mentioned above, energy source 20 provides a propulsion force that acts on drive rod 22 to propel rod 22 and cutting element 30 away from launch barrel 12 in order to effect an amputation. In general, cutting element 30 with its cutting blade 34 must be driven at a velocity in the range of 300-1000 feet per second in order to effect an amputation. At these velocities, cutting blade 34 in its prescribed V-shape begins cutting soft-tissue just before an impact and cutting force is applied to hard/bone tissue by the regions of cutting blade 34 near its vertex 38. To achieve such velocities, energy source 20 must apply its peak launch/propulsion force to end 26 of drive rod 22 very quickly. More specifically, the peak force generated by energy source 20 must be achieved within 0.5 milliseconds. Accordingly, energy source 20 can be a conventional or specially-designed energetic energy source such as a gas-generating cartridge that generates or emits pressurized gas when activated to propel drive rod 22 from bore 14. A variety of activation mechanisms (not shown) can be used to activate energy source 20 without departing from the scope of the present invention.

Figure 3:
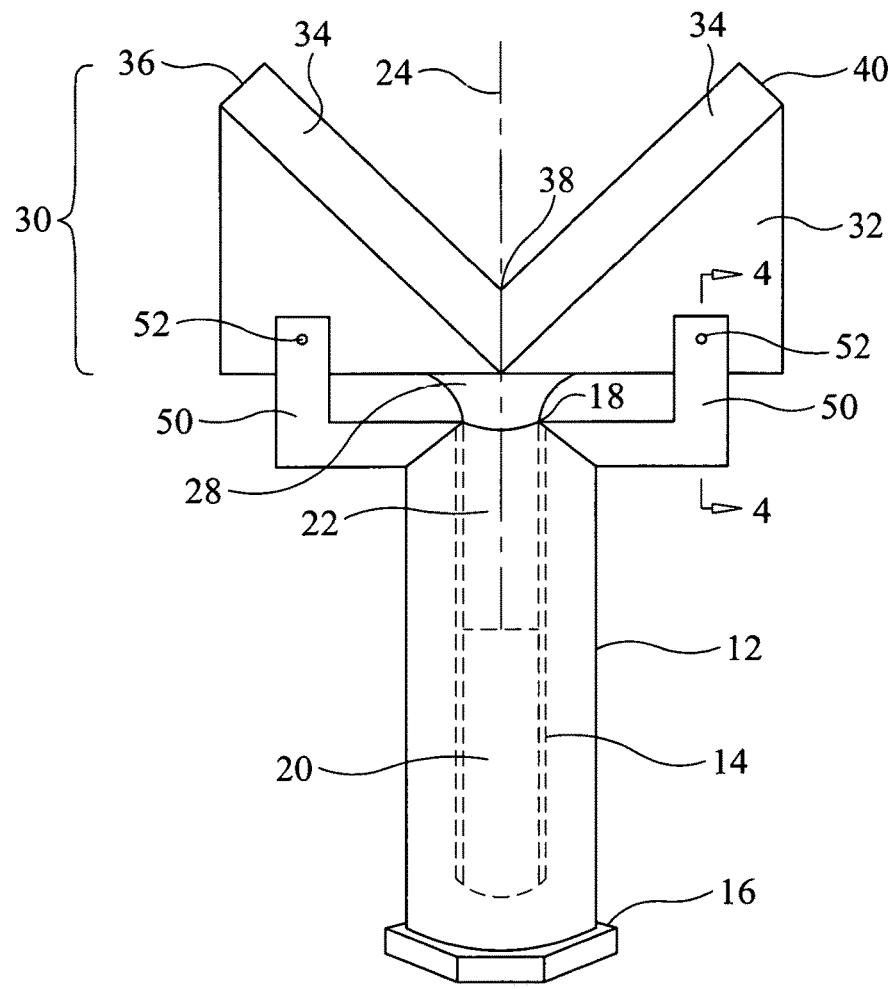
FIG. 3 is a perspective view of an amputation system in accordance with another embodiment of the present invention.
Figure 4:
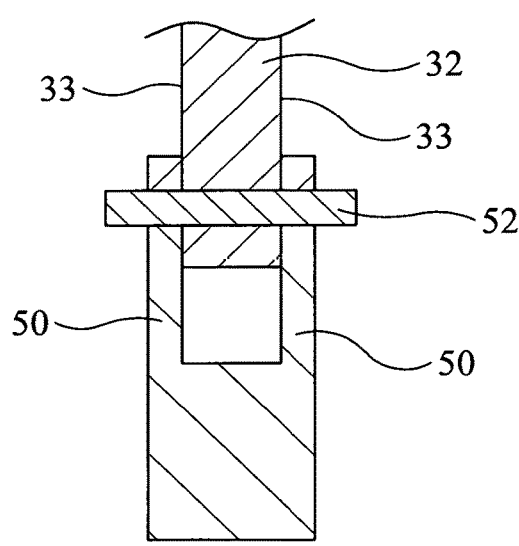
FIG. 4 is a cross-sectional view of the amputation system's cutting element and travel guide take along line 4-4 in FIG. 3.

The size and/or operational velocity of an amputation system of the present invention could require the use of a guiding mechanism to assure that drive rod 22 and cutting element 30 travel in a direction coincident with the drive rod's longitudinal axis 24 as drive rod 22 is propelled from bore 14. By way of a non-limiting example, one such launch travel guide will now be described with simultaneous reference to FIGS. 3 and 4. In the illustrated exemplary embodiment, guide arms 50 are rigidly coupled to launch barrel 12 and extend over opposing faces 33 of support body 32. Shear pins 52 extend through each pair of guide arms 50 and support body 32. Shear pins 52 retain cutting element 30 in place prior to launch. At launch, shear pins 52 fail as guide arms 50 serve to guide the travel of cutting element 30 during its initial movement away from launch barrel 12.

The advantages of the present invention are numerous. The amputation system is a simple and compact device ideally suited for field amputations. The system's unique cutting blade design combined with its high-velocity delivery will assure quick and clean limb amputations thereby reducing patient trauma and improving patient safety. No external power sources are required thereby making the amputation system usable in any field environment.

Although the invention has been described relative to a specific embodiment thereof, there are numerous variations and modifications that will be readily apparent to those skilled in the art in light of the above teachings. It is therefore to be understood that, within the scope of the appended claims, the invention may be practiced other than as specifically described.

Finally, any numerical parameters set forth in the specification and attached claims are approximations (for example, by using the term "about") that may vary depending upon the desired properties sought to be obtained by the present invention. At the very least, and not as an attempt to limit the application of the doctrine of equivalents to the scope of the claims, each numerical parameter should be at least construed in light of the number of significant digits and by applying ordinary rounding.

What is claimed is:

1. An amputation system, comprising:
   a cutting element being comprised of a medical grade material, said cutting element includes a cutting blade traversing a V-shape and has a blade taper angle in a range of 15-25°, said V-shape includes a vertex and has an angle in a range of 90-120°;
   a rod rigidly being coupled to said cutting element, said rod includes a longitudinal axis aligned with said vertex and bisects said angle, said rod includes an outboard end;
   a barrel comprising a bore for receiving at least a portion of said rod therein, wherein said outboard end of said rod resides in said bore;
   an energetic energy source being positioned in said bore adjacent to said outboard end of said rod for generating a pressure force that is incident on said outboard end of said rod, wherein said pressure force peaks within 0.5 milliseconds, and propels said rod and said cutting element away from said barrel at a velocity in a range of 300 to 1000 feet per second; and
   a travel guide being uncoupled from said cutting element as said cutting element is propelled away from said barrel.

2. The amputation system as in claim 1, wherein a cross-section of said cutting blade taken perpendicular to said cutting blade is constant along said V-shape.

3. The amputation system as in claim 1, further comprising a travel guide being coupled to said barrel and to said cutting element, wherein said travel guide guides said cutting element as said rod and said cutting element are propelled away from said barrel, and wherein said vertex travels in a direction aligned with said longitudinal axis of said rod.

4. The amputation system as in claim 1, wherein said pressure force is generated by a pressurized gas.

5. An amputation system, comprising:
   a cutting element including a cutting blade traversing a V-shape, said V-shape includes a vertex and has an angle in a range of 90-120°;
   a rod rigidly being coupled to said cutting element, said rod includes a longitudinal axis aligned with said vertex and bisects said angle, and wherein said rod includes an outboard end;
   a barrel including a bore for receiving at least a portion of said rod therein, wherein said outboard end of said rod resides in said bore;
   an energetic energy source being positioned in said bore adjacent to said outboard end of said rod for generating a pressure force that is incident on said outboard end of said rod, wherein said pressure force peaks within 0.5 milliseconds, and propels said rod and said cutting element away from said barrel at a velocity in a range of 300 to 1000 feet per second;
   a travel guide being coupled to said barrel for guiding said cutting element as said rod and said cutting element are being propelled away from said barrel, wherein said vertex travels in a direction aligned with said longitudinal axis of said rod; and shear pins for coupling said cutting element to said travel guide, wherein said shear pins fail as said cutting element is propelled away from said barrel.

6. The amputation system as in claim 5, wherein said cutting blade has a blade taper angle in a range of 15-25°.

7. The amputation system as in claim 5, wherein said cutting element is fabricated from a medical grade material.

8. The amputation system as in claim 5, wherein a cross-section of said cutting blade taken perpendicular to said cutting blade is constant along said V-shape.

9. The amputation system as in claim 5, wherein said pressure force is generated by a pressurized gas.

10. An amputation system, comprising:

a cutting element including a cutting blade traversing a V-shape, said cutting element includes a cutting blade traversing the V-shape and has a blade taper angle in a range of 15-25°, and said V-shape includes a vertex and has an angle in a range of 90-120°;

a rod rigidly being coupled to said cutting element, said rod includes a longitudinal axis aligned with said vertex and bisects said vertex angle, and wherein said rod includes an outboard end;

a barrel including a bore for receiving at least a portion of said rod therein, wherein said outboard end of said rod resides in said bore;

an energetic energy source being positioned in said bore adjacent to said outboard end of said rod for generating a pressure force that is incident on said outboard end of said rod, wherein said pressure force peaks within 0.5 milliseconds, and propels said rod and said cutting element away from said barrel at a velocity in a range of 300 to 1000 feet per second;

a travel guide being coupled to said barrel for guiding said cutting element as said rod and said cutting element are being propelled away from said barrel, wherein said vertex travels in a direction aligned with said longitudinal axis of said rod; and shear pins for coupling said cutting element to said travel guide, wherein said shear pins fail as said cutting element is propelled away from said barrel.

* * * * *